United States Patent
Yamanishi et al.

(10) Patent No.: US 10,006,084 B2
(45) Date of Patent: Jun. 26, 2018

(54) METHODS TO REDUCE EVAPORATION DURING ELEVATED TEMPERATURE

(71) Applicant: SAKURA FINETEK U.S.A., INC., Torrance, CA (US)

(72) Inventors: Douglas T. Yamanishi, Redondo Beach, CA (US); Clifford Hom, Redondo Beach, CA (US); Amit D. Shah, Rancho Palos Verdes, CA (US)

(73) Assignee: Sakura Finetek U.S.A., Inc., Torrance, CA (US)

( * ) Notice: Subject to any disclaimer, the term of this patent is extended or adjusted under 35 U.S.C. 154(b) by 120 days.

(21) Appl. No.: 14/701,043

(22) Filed: Apr. 30, 2015

(65) Prior Publication Data

US 2016/0319337 A1    Nov. 3, 2016

(51) Int. Cl.
G01N 33/53    (2006.01)
C12Q 1/68     (2018.01)
C12Q 1/6841   (2018.01)

(52) U.S. Cl.
CPC ....... C12Q 1/6841 (2013.01); G01N 33/5306 (2013.01)

(58) Field of Classification Search
CPC ............ C12Q 1/6841; G01N 33/5306
USPC ............ 435/6.12, 6.1; 436/8
See application file for complete search history.

(56) References Cited

U.S. PATENT DOCUMENTS

| | | | |
|---|---|---|---|
| 5,422,277 A | 6/1995 | Connelly et al. | |
| 5,849,517 A | 12/1998 | Ryan | |
| 5,888,733 A | 3/1999 | Hyldig-Nielsen et al. | |
| 6,017,725 A | 1/2000 | Hoffmann et al. | |
| 6,337,189 B1 | 1/2002 | Ryan | |
| 6,458,322 B1 | 10/2002 | Harris | |
| 6,531,317 B2 | 3/2003 | Guirguis et al. | |
| 6,855,552 B2 | 2/2005 | Towne et al. | |
| 6,855,559 B1 | 2/2005 | Christensen et al. | |
| 7,550,298 B2 | 6/2009 | Towne et al. | |
| 8,309,302 B2 | 11/2012 | Jaekel et al. | |
| 2004/0054160 A1* | 3/2004 | Pal | C12Q 1/6806 536/24.3 |
| 2007/0048770 A1 | 3/2007 | Jaekel et al. | |
| 2014/0186882 A1 | 7/2014 | Berberich et al. | |
| 2014/0234844 A1 | 8/2014 | Matthiesen | |
| 2014/0242595 A1 | 8/2014 | Yu et al. | |
| 2016/0003716 A1 | 1/2016 | Torres et al. | |

FOREIGN PATENT DOCUMENTS

| | | |
|---|---|---|
| WO | WO-2012055981 | 5/2012 |
| WO | WO-2014144663 | 9/2014 |

OTHER PUBLICATIONS

Sakura Finetek U.S.A., "International search report and written opinion", PCT Application No. US2016/027945, (dated Jun. 14, 2016).

Van Gijlswijk, R. P., et al., "Improved localization of fluorescent pyramids for fluorescence in situ hybridization suing dextran sulfate and polyvinyl alcohol", Journal of Histochemistry and Cytochemistry, vol. 44, No. 4, (Apr. 1, 1996), 389-392.

* cited by examiner

*Primary Examiner* — Jezia Riley
(74) *Attorney, Agent, or Firm* — Womble Bond Dickinson (US) LLP

(57) ABSTRACT

A method including contacting a tissue or cellular sample with a reagent including an evaporation reducing agent(s) having the general formula $X_1$—R—$X_2$, wherein R is an alkyl, alkenyl, alkynyl or an aromatic moiety of 1 or more carbon atoms that may be substituted with an oxygen, nitrogen or sulfur and $X_1$ and $X_2$ are independently selected to be moiety that is susceptible to hydrogen bonding and processing the tissue or cellular sample. A reagent used in the processing of a tissue or cellular sample with the reagent containing an evaporation reducing agent.

18 Claims, No Drawings

METHODS TO REDUCE EVAPORATION DURING ELEVATED TEMPERATURE

FIELD

Assay reagent.

BACKGROUND

Immunohistochemical assays and assay techniques based on in situ hybridization are widely used in medical diagnostics such as to diagnose abnormal cells such as those found in cancerous tumors or to diagnose another disease. Many assays involve the addition of heat to the sample, such as to a sample in a reagent on a slide. Assay steps at elevated temperatures can cause substantial evaporation of assay reagents. When small volumes are used, sample denaturation, hybridization, wash and aging steps and the resulting assay can be compromised by evaporation.

DETAILED DESCRIPTION

A reagent and a method of use of a reagent including an evaporation reducing agent in an aqueous solution operable to reduce evaporation of the reagent in processing of a tissue or cellular sample is disclosed. Representative processing for which a reagent as described finds use include, but are not limited to, dewaxing, cell conditioning/antigen retrieval/cell aging, peroxide/phosphatase block, probe denature, probe hybridization, washing, linker hybridization, antibody incubation, probe detection, chromogen precipitation and counterstain involving an elevated temperature step (e.g. an elevated temperature step in an in situ hybridization procedure). The solution can representatively be used in denaturation, wash or hybridization steps of a nucleic acid (single or double stranded probe) hybridization assay or in an incubation, antigen retrieval or a wash step using an antibody in immunohistochemical or immunocytochemical staining A suitable reagent may include other components such as a detergent/surfactant which helps with solution spreading in a hybridization solution reagent. In one embodiment, a suitable amount of an evaporation reducing agent in a reagent operable for tissue or cellular processing is an amount that will limit a loss of the reagent due to evaporation to 20 percent or less under industry acceptable reagent processing conditions such as subjecting a hybridization solution to an elevated temperature between 25° C. and 50° C. for 10 minutes to 24 hours (e.g., a hybridization or incubation process) or to an elevated temperature of between 60° C. and 100° C. for two to ninety minutes (e.g., a denaturing or antigen retrieval process). In one embodiment, a suitable amount of an evaporation reducing agent is in the range of 11 percent to 60 percent by volume of a regent composition (e.g., solution).

In one embodiment, a reagent (composition) includes an effective evaporation reducing amount of an evaporation reducing agent comprising the formula of General Formula I:

$$X_1\text{—}R\text{—}X_2,$$

wherein R is an alkyl, an alkenyl, an alkynyl or an aromatic moiety of one or more carbon atoms (e.g., one to six carbon atoms in one embodiment and one to four carbon atoms in another embodiment where it is appreciated that if R is a moiety of one carbon, R is an alkyl) that may be substituted with oxygen atom, sulfur atom and/or or nitrogen atom (e.g., —OH, —SH, or —NH$_2$ is substituted for a hydrogen atom of one or more hydrocarbons defining the alkyl, alkenyl, alkynyl or aromatic) or that may be interrupted with an oxygen atom, a sulfur atom and/or a nitrogen atom (e.g., —C—O—C—, —C—SH—C—, —C—NH—C—). An alkyl moiety is an alkane containing open points of attachment for connection for $X_1$ and $X_2$. An alkenyl moiety is an alkene containing open points of attachment for connection for $X_1$ and $X_2$. An alkynyl moiety is an alkyne containing open points of attachment for connection to $X_1$ and $X_2$. Representative alkyls include straight or branched chain alkyls (e.g., methyl, ethyl, propyl, isopropyl) which may or may not be further substituted. Representative alkenyls include straight or branched chain alkenyls (e.g., ethenyl, propenyl, isopropenyl). Representative alkynyls include straight or branched chain alkynyls which may or may not be further substituted (e.g., ethynyl, propynyl, isopropynyl). An aromatic moiety is an unsaturated ring of atoms that is stabilized by an interaction of the bonds forming the ring. An example of an aromatic moiety is benzyl. Examples of interrupted aromatic moieties are pyridine (interrupted with a nitrogen atom); furan (interrupted with an oxygen atom); and thiophene (interrupted with a sulfur atom).

$X_1$ and $X_2$ in General Formula I are independently selected to be a moiety where one or both are susceptible to hydrogen bonding and/or contains an electronegative atom. Representative moieties for $X_1$ and $X_2$ will include functional groups that are capable of hydrogen bonding such as but not limited to hydroxyl moieties (—OH); carbonyl moieties (—CO); amine moieties (—NH$_2$); aldehyde moieties (—CHO); halogen moieties (—Y, where Y is Cl$^-$, F$^-$, Br$^-$ or I$^-$); ether moieties (—OR$^1$, where R$^1$ is an alkyl (e.g., an alkyl of one to six carbon atoms) that may be substituted with a moiety that is susceptible or capable of hydrogen bonding and/or contains an electronegative atom); carboxyl moieties (—COOR$^2$, where R$^2$ is a hydrogen atom or an alkyl (e.g., an alkyl of one to six carbon atoms) that may be substituted with a moiety that is susceptible or capable of hydrogen bonding and/or contains an electronegative atom); and amide moieties (—CONR$^3$R$^4$, where R$^3$ and R$^4$ are independently selected from a hydrogen atom or an alkyl (e.g., an alkyl of one to six carbon atoms) that may be substituted with a moiety that is susceptible or capable of hydrogen bonding and/or contains an electronegative atom). Representative of substitution moieties that are susceptible or capable of hydrogen bonding for the noted alkyls associated with ether, carboxyl and amide moieties for $X_1$ and $X_2$ (R$^1$, R$^2$, R$^3$ and R$^4$) include hydroxyl, carbonyl, amine, aldehyde, halogen, ether, carboxyl and amide moieties.

Examples of suitable evaporation reducing agents having General Formula I include ethylene glycol, glycine, serine, isoethionic acid, ethanolamine, polyethylene glycol and 1,3-propanediol. In one embodiment, R is not substituted or interrupted. Representative of an evaporation reducing agent where R is not substituted or interrupted is ethylene glycol (HO(CH$_2$)$_2$OH) where R is ethyl and each of $X_1$ and $X_2$ is a hydroxyl moiety. An example of an evaporation reducing agent where $X_2$ is a primary amide that is further substituted with a moiety susceptible or capable of hydrogen bonding is H$_2$N-(CH$_2$)$_3$—NH(CH$_2$)$_2$COOH, where R is —(CH$_2$)$_3$—; $X_1$ is —NH$_2$ and $X_2$ is —NH(CH$_2$)$_2$COOH. In one embodiment, a suitable reagent includes one or more evaporation reducing agents having the formula of General Formula I (e.g., a reagent includes a combination of two or three evaporation reducing agents and having the formula of General Formula I).

An evaporation reducing agent may be in a molecular free form (a molecule) or an acceptable salt thereof (a compound) or ionic liquid. An example of a salt is a hydrohalide salt of the molecule such as a hydrochloride salt.

In one embodiment, an evaporation reducing agent as a solute reduces the vapor pressure of a solution upon its mixing with one or more other reagents. Such solute could be a molecule, an ionic salt, an ionic liquid, a non-ionic agent that may exhibit complete or partial solubility or miscibility with water and is capable of reducing a partial pressure of an aqueous solution to which it is mixed or otherwise introduced. Additionally, an evaporation reducing agent may or may not form an azeotropic mixture with water. If an evaporation reducing agent does form an azeotropic mixture with water, the solute, in one embodiment, forms a negative azeotrope with water.

Generally speaking, when a solvent and a solute are mixed in this context, a resulting chemical potential of the solvent is lowered so that a partial pressure of the solvent molecules is reduced and, relative to a solvent-only solution, has a reduced tendency to transition into gas phase. Representatively, a partial pressure of water in an aqueous solution where a solute is a nonvolatile evaporation reducing agent will be reduced which would result in elevation of a boiling point of the mixture as well as a reduction in evaporation at the surface.

Hydrogen bonding can occur when in a molecule, a hydrogen atom is attached to an electronegative atom such as an oxygen, nitrogen or fluorine atom and the molecule comes in proximity with an electropositive atom. The electrostatic attraction of this nature has a strength on the order of 5-30 kJ/mol which is stronger than Van der Waals attraction but weaker than covalent or ionic bonding.

In one embodiment, an evaporation reducing agent is mixed as a solute with water to reduce a vapor pressure of the water by creating a solution where a partial pressure of the water is reduced such that an assay (e.g., an immunohistologic assay) can be carried out more efficiently than if the partial pressure was not lowered. In one embodiment, a solute is selected such that there is no or minimum residue left behind which may interfere with an assay known to a person skilled in the art, In one embodiment, a reagent operable for use in processing a cellular or tissue sample is prepared by combining a base reagent and an evaporation reducing agent. Additional components may also be combined in a suitable composition. The reagent can be added to an aqueous buffer solution to reduce evaporation during elevated temperatures. In one embodiment, the evaporation reducing agent is combined in an amount to limit any loss of the combination due to evaporation to 20 percent or less and, in another embodiment, to 10 percent or less. Representatively, an evaporation reducing agent or combination of reducing agents is/are present in a composition in an amount between 11 percent and 60 percent by volume or an amount between 1 percent and 60 percent of the reducing agent is a non-glycol-containing compound or a combination of reducing agents. Following a combination of a base reagent, evaporation reducing agent and any other components, the composition may be mixed.

In one embodiment, a method operable in processing of a paraffin-free or deparaffinized tissue or cellular sample for use in an assay at an elevated temperature is disclosed. In one embodiment, a method is operable to reduce evaporation of any aqueous based processing reagent. The method includes contacting a tissue or cellular sample with a reagent including an evaporation reducing agent (e.g., as a solute) having the formula of General Formula I:

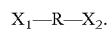

Such contact includes applying the reagent to a sample on a slide. Following contacting the sample with the reagent, the sample may be processed according to techniques known in the art.

In one embodiment, a method operable in processing of a paraffin-free or deparaffinized tissue or cellular sample for use in an assay at an elevated temperature is disclosed. In one embodiment, a method is operable to reduce evaporation of any aqueous based processing reagent by adding a solute to a solvent. The resulting chemical potential of the solvent is lowered so that the partial pressure of the solvent molecules is reduced and they have lesser tendency to turn into gas phase. Partial pressure of water in an aqueous solution where solute is a nonvolatile substance is reduced which would result in elevation of boiling point as well as reduction in evaporation at the surface.

EXAMPLES

Example 1: Volume Loss Due to Evaporation During Oligonucleotide Hybridization at Different Hybridization Temperatures 400 µl of hybridization solution (reagent) was applied to each of six sample slides and the slides were individually heated to different temperatures for 30 minutes. It was observed that evaporation occurred on the slide with hybridization solution during the hybridization step.

TABLE 1

| Effect of temperature on evaporation | |
| --- | --- |
| Hybridization Temperature (° C.) | Ave volume loss due to evaporation (µl) |
| 25 | 7.5 |
| 35 | 37.5 |
| 37 | 50.0 |
| 39 | 47.5 |
| 41 | 50.0 |
| 43 | 55.0 |

Example 2: Reducing Evaporation During Oligonucleotide Hybridization by Different Reagents 400 µl of hybridization solution (reagent) with different evaporation reducing agents was applied to respective sample slides and heated to 43° C. for 30 minutes. One sample slide included a hybridization solution with no evaporation reducing agent. It was observed that a significantly greater evaporation of the hybridization solution occurred with the sample slide containing a hybridization solution without an evaporation reducing agent during the 43° C. hybridization step but was reduced with the addition of an evaporation reducing agent.

TABLE 2

Ability of added agent to hybridization solution (reagent) to reduce evaporation

| Reagent | Avg volume loss (µl) |
| --- | --- |
| No addition | 55.0 |
| 20% Ethylene Glycol | 20.0 |
| 20% Propylene Glycol | 45.0 |
| 20% Glycerol | 42.5 |
| 20% Polyethylene Glycol | 15.0 |

Example 3: Reducing Evaporation Using Different Concentrations of Ethylene Glycol During Hybridization 400 µl of hybridization solution (reagent) having different concentrations of an evaporation reducing agent of ethylene glycol was applied to respective sample slides and heated to 43° C. for 30 minutes. For comparison, 400 µl of hybridization solution without ethylene glycol was also applied to a sample slide and heated to 43° C. for 30 minutes. It was observed that evaporation was reduced with the addition of ethylene glycol to the hybridization solution. The assay performance for the hybridization solution containing ethylene glycol was found to be similar to hybridization solution without ethylene glycol.

TABLE 3

Reduction in volume loss in % ethylene glycol (EG) in hybridization solution

| | | Comparison to Starting Volume | |
| --- | --- | --- | --- |
| % EG | Starting vol (µl) | Avg evaporatiion (µl) | % Evaporation |
| 0% | 400 | 48 | 12% |
| 7% | 400 | 28 | 7% |
| 14% | 400 | 18 | 4% |
| 20% | 400 | 13 | 3% |
| 27% | 400 | 10 | 2% |
| 33% | 400 | 0 | 0% |
| 40% | 400 | 0 | 0% |

Example 4: Reproducibility in Reducing Evaporation Volume Loss During Hybridization 400 µl of hybridization solution with specific concentrations of an evaporation reducing agent of ethylene glycol was applied to each sample slide and heated to 43° C. for 30 minutes. For comparison, 400 µl of hybridization solution was applied to each sample slide and heated to 43° C. for 30 minutes. It was observed that evaporation was reduced with the addition of ethylene glycol to the hybridization solution.

TABLE 4

Reduction in evaporation due to addition of ethylene glycol

| | oligonucleotide hybridization solution with 0% ethylene glycol | | oligonucleotide hybridization solution with 20% ethylene glycol | |
| --- | --- | --- | --- | --- |
| Slide | Starting vol (µl) | Evaporation (µl) | Starting vol (µl) | Evaporation (µl) |
| 1 | 400 | 45 | 400 | 12 |
| 2 | 400 | 50 | 400 | 15 |
| 3 | 400 | 45 | 400 | 15 |
| 4 | 400 | 55 | 400 | 17 |
| 5 | 400 | 40 | 400 | 15 |
| 6 | 400 | 50 | 400 | 10 |
| 7 | 400 | 50 | 400 | 12 |
| 8 | 400 | 45 | 400 | 15 |
| 9 | 400 | 50 | 400 | 12 |
| 10 | 400 | 45 | 400 | 12 |
| | Avg | 48 | Avg | 14 |

Example 5: Reduction in Evaporation During Denaturation

About 400 µl of hybridization solution with an evaporation reducing agent of 20 percent ethylene glycol was applied to each sample slide and heated to 92-98° C. for 2 minutes. For comparison, about 400 µl of hybridization solution without ethylene glycol was applied to each sample slide and heated to 92-98° C. for 2 minutes. It was observed that evaporation was reduced with the addition of ethylene glycol to the hybridization solution.

TABLE 5

Reduction in evaporation with addition of ethylene glycol to hybridization solution during denaturation.

| | | oligonucleotide hybridization solution with 0% ethylene glycol | | | oligonucleotide hybridization solution with 20% ethylene glycol | | |
| --- | --- | --- | --- | --- | --- | --- | --- |
| Temp (° C.) | Time (min) | Starting vol (µl) | Evaporation (µl) | Avg. loss due to Evaporation | Starting vol (µl) | Evaporation (µl) | Avg. loss due to Evaporation |
| 92 | 2 | 400 | 60 | 15% | 400 | 15 | 4% |
| 92 | 2 | 400 | 65 | | 400 | 17 | |
| 92 | 2 | 400 | 50 | | 400 | 15 | |
| 95 | 2 | 400 | 60 | 16% | 400 | 30 | 7% |
| 95 | 2 | 400 | 70 | | 400 | 30 | |
| 95 | 2 | 400 | 65 | | 400 | 25 | |
| 98 | 2 | 400 | 80 | 19% | 400 | 33 | 8% |
| 98 | 2 | 400 | 75 | | 400 | 30 | |
| 98 | 2 | 400 | 75 | | 400 | 30 | |

Example 6: Reduction in Evaporation During Antibody Incubation Step

About 400 µl of primary antibody diluent (reagent) with an evaporation reducing agent of 20 percent ethylene glycol was applied to each sample slide and incubated at a specific temperature for 30 minutes. For comparison, about 400 µl of primary antibody diluent without ethylene glycol was applied to each sample slide and incubated at a specific temperature for 30 minutes. It was observed that evaporation was reduced with the addition of ethylene glycol to the antibody diluent.

TABLE 6

Reduction in evaporation with addition of ethylene glycol to antibody diluent

| Temp (° C.) | Primary antibody diluent with 0% ethylene glycol | | | Primary antibody diluent with 20% ethylene glycol | | |
|---|---|---|---|---|---|---|
| | Starting vol (µl) | Evaporation (µl) | Avg. loss due to Evaporation | Starting vol (µl) | Evaporation (µl) | Avg. loss due to Evaporation |
| 20 | 400 | 0 | 0% | 400 | 0 | 0% |
| 20 | 400 | 0 | | 400 | 0 | |
| 25 | 400 | 3 | 1% | 400 | 0 | 0% |
| 25 | 400 | 5 | | 400 | 0 | |
| 31 | 400 | 30 | 9% | 400 | 5 | 1% |
| 31 | 400 | 40 | | 400 | 5 | |
| 37 | 400 | 60 | 17% | 400 | 3 | 1% |
| 37 | 400 | 75 | | 400 | 5 | |
| 43 | 400 | 95 | 23% | 400 | 20 | 6% |
| 43 | 400 | 90 | | 400 | 25 | |

Example 7: Reducing Evaporation During Oligonucleotide Hybridization by Different Reagents 400 µl of hybridization solution with different evaporation reducing agents was applied to respective sample slides and heated to 43° C. for 30 minutes. A hybridization solution containing no evaporation reducing agent was also applied to a sample slide. It was observed that evaporation occurred in the slide with hybridization solution during the 43° C. hybridization step but was reduced with the addition of specific reagent.

TABLE 7

Ability of added evaporation reducing agent to hybridization solution to reduce evaporation

| Evaporation Reducing Agent | Avg volume loss (µl) |
|---|---|
| No addition | 57.5 |
| 20% ethylene glycol | 20 |
| 20% glycine | 27.5 |
| 20% serine | 17.5 |
| 20% isoethionic acid | 25 |
| 20% ethanolamine | 17.5 |
| 20% 1,3-propanediol | 22.5 |

Example 8: Reducing Evaporation Using Ethylene Glycol During Hybridization at Different Temperatures 400 µl of hybridization solution (reagent) with ethylene glycol was applied to respective sample slides and heated to 35, 37 or 40° C. for 120 minutes. For comparison, 400 µl of hybridization solution without ethylene glycol was also applied to a sample slide and heated to 40° C. for 120 minutes. It was observed that evaporation was reduced with the addition of ethylene glycol to the hybridization solution. The assay performance for the hybridization solution containing ethylene glycol at different hybridization temperatures was found to be similar to hybridization solution without ethylene glycol.

Reagents
Hybridization Solution

| Chemical | Final conc. |
|---|---|
| SSC | 2 x |
| Tris-HCl | 10 mM |
| Dextran sulfate | 10% |
| Denhardt's solution | 2 x |
| Tween | 0.05% |
| Triton | 0.10% |
| Salmon sperm DNA | 50 µg/ml |
| Evaporation reducing agent | varied |
| water | varied |

Primary Antibody Diluent

| Chemical | Final conc. |
|---|---|
| Sodium Azide | 0.05% |
| Sodium Chloride | 300 mM |
| Sodium Phosphate Dibasic | 8 mM |
| Potassium Phosphate monobasic | 2 mM |
| Green Color Dye | 0.025% |
| BSA Powder | 1% |
| Tris Base | 10 mM |
| Tris HCl | 40 mM |
| Tween | 0.05% |
| Triton | 0.1% |
| Evaporation reducing agent | varied |
| water | varied |

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below. In other instances, well-known structures, devices, and operations have been shown in block diagram form or without detail in order to avoid obscuring the understanding of the description. Where considered appropriate, reference numerals or terminal portions of reference numerals have been repeated among the figures to indicate corresponding or analogous elements, which may optionally have similar characteristics.

It should also be appreciated that reference throughout this specification to "one embodiment", "an embodiment", "one or more embodiments", or "different embodiments", for example, means that a particular feature may be included in the practice of the invention. Similarly, it should be appreciated that in the description various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

The invention claimed is:

1. A method comprising:
contacting a tissue or cellular sample with a composition of a hybridization solution or a primary antibody diluent solution, wherein the hybridization solution or the primary antibody diluent solution comprises a detergent and at least one evaporation reducing agent having the general formula:

$$X_1-R-X_2,$$

wherein R is an alkyl moiety, alkenyl moiety, alkynyl moiety or aromatic moiety that may be substituted or interrupted with an oxygen, sulfur or nitrogen atom and $X_1$ and $X_2$ are independently selected to be moiety that comprises an electronegative atom or is susceptible to hydrogen bonding and wherein the at least one evaporation reducing agent is present in an amount of greater than 20 percent by volume when the at least one evaporation reducing agent is a non-glycol-containing agent or a combination of more than one evaporation reducing agent or an amount greater than 30 percent by volume when the at least one evaporation reducing agent is a glycol-containing agent; and processing the tissue or cellular sample.

2. The method of claim 1, wherein the evaporation reducing agent is present in an amount up to 60 percent by volume.

3. The method of claim 1, wherein the processing comprises an elevated temperature.

4. The method of claim 1, wherein the processing comprises a hybridization.

5. The method of claim 1, wherein the processing comprises a dehybridization.

6. The method of claim 1, wherein the processing comprises a wash step.

7. The method of claim 1, wherein the processing comprises an antigen binding.

8. The method of claim 1, wherein the processing comprises an antigen retrieval, cell conditioning or cell aging.

9. The method of claim 1, wherein $X_1$ and $X_2$ are independently selected such that at least one contains one or more from group consisting of hydroxyl moieties, carbonyl moieties, amine moieties, aldehyde moieties, halogen moieties, ether moieties, carboxyl moieties and amide moieties.

10. The method of claim 9, wherein $X_1$ and $X_2$ are independently selected to include at least a moiety selected from the group consisting of —OH, —CHO, —OR$^1$, —NH$_2$, —COOR$^2$ and —CONH$_2$, wherein R$^1$ is an alkyl and R$^2$ is a hydrogen atom or an alkyl.

11. The method of claim 1, wherein R is an alkyl comprising two or more carbon atoms of which one or more may or may not be substituted with O, N or S.

12. The method of claim 1, wherein the at least one evaporation reducing agent comprises ethylene glycol.

13. The method of claim 1, wherein the at least one evaporation reducing agent comprises glycine, serine, isoethionic acid, ethanolamine, glycerol, polyethylene glycol, 1,3-propanediol or a combination of these agents.

14. The method of claim 1, wherein the at least one evaporating reducing agent comprises a combination of evaporation reducing agents.

15. A reagent operable for use in processing of a tissue or cellular sample, the reagent comprising a composition of a hybridization solution or a primary antibody diluent solution, wherein the hybridization solution or the primary antibody diluent solution comprises a detergent and an evaporation reducing agent present in an amount of greater than 20 percent by volume when the evaporation reducing agent is a non-glycol-containing agent or a combination of more than one evaporation reducing agent or an amount greater than 30 percent by volume when the evaporation reducing agent is a glycol-containing agent having the general formula:

$$X_1-R-X_2$$

wherein R is an alkyl moiety, alkenyl moiety or alkynyl moiety that may be substituted or interrupted with an oxygen, sulfur or nitrogen atom and $X_1$ and $X_2$ are independently selected to be a moiety that comprises an electronegative atom or is susceptible to hydrogen bonding.

16. The reagent of claim 15, wherein the evaporation reducing agent is present in an amount up to 60 percent by volume.

17. The reagent of claim 15, wherein $X_1$ and $X_2$ are independently selected so that at least one contains one or more from group of hydroxyl moieties, carbonyl moieties, amine moieties, aldehyde moieties, halogen moieties, ether moieties, carboxyl moieties and amide moieties.

18. The reagent of claim 15, wherein the evaporation reducing agent comprises a combination of evaporation reducing agents.

* * * * *